United States Patent [19]

Borner et al.

[11] Patent Number: 4,772,288

[45] Date of Patent: Sep. 20, 1988

[54] METHOD FOR PRODUCING IMPLANTABLE LIGAMENT AND TENDON PROSTHESES AND PROSTHESES PRODUCED THEREBY

[76] Inventors: William H. Borner, 24692 Priscilla Dr., Dana Point, Calif. 92629; Marcel E. Nimni, 2800 Neilson Way, #908, Santa Monica, Calif. 90405; Rudy C. Shepard, 264 Via Pata, Coto De Casa, Calif. 92679

[21] Appl. No.: 62,027

[22] Filed: Jun. 15, 1987

[51] Int. Cl.$^4$ ............................................. A61L 17/00
[52] U.S. Cl. ........................................... 8/94.11; 623/1; 623/2
[58] Field of Search ................... 8/94.11; 623/1, 2

[56] References Cited

U.S. PATENT DOCUMENTS

| | | | |
|---|---|---|---|
| 2,640,752 | 6/1953 | Davis et al. | 8/94.11 |
| 3,114,593 | 12/1963 | Griset et al. | 18/54 |
| 3,304,557 | 2/1967 | Polansky | 623/1 |
| 3,526,228 | 9/1970 | Lyng | 128/334 |
| 3,551,560 | 12/1970 | Thiele | 424/95 |
| 4,378,224 | 3/1983 | Nimni et al. | 8/94.11 |
| 4,383,832 | 5/1983 | Fraefel et al. | 8/94.11 |
| 4,481,009 | 11/1984 | Nashef | 8/94.11 |

FOREIGN PATENT DOCUMENTS 164060 6/1953 Australia .................... 87.4/47.2

WO85/05274 12/1985 PCT Int'l Appl. .

Primary Examiner—Paul Lieberman
Assistant Examiner—John F. McNally
Attorney, Agent, or Firm—Allan O. Maki

[57] ABSTRACT

A method of making implantable ligament and tendon prostheses from natural collagen-containing tissues is described. The tissues used are those wherein the collagen fibers are aligned in one direction such as in ligaments or tendons. The method comprises disrupting the interfibrillar matrix physically by mechanical means such as a roller or rollers in order to generate an expanded network of fibers that are more easily further treated chemically and which also generate a more favorable substrate for tissue ingrowth after implantation. Prostheses made from separated collagen fiber bundles which retain their natural configuration and length (as opposed to reconstituted collagen), exhibit improved softness and flexibility when compared with prostheses made from conventional chemically fixed (e.g., glutaraldehyde cross-linked) tendons which have not been separated as described herein. Another implementation of the developed new technology allows for the formation of composites between the dissociated collagen fibers involving two or more tissues or between collagen and synthetic fibers. These composites can also include absorbable materials.

16 Claims, 1 Drawing Sheet

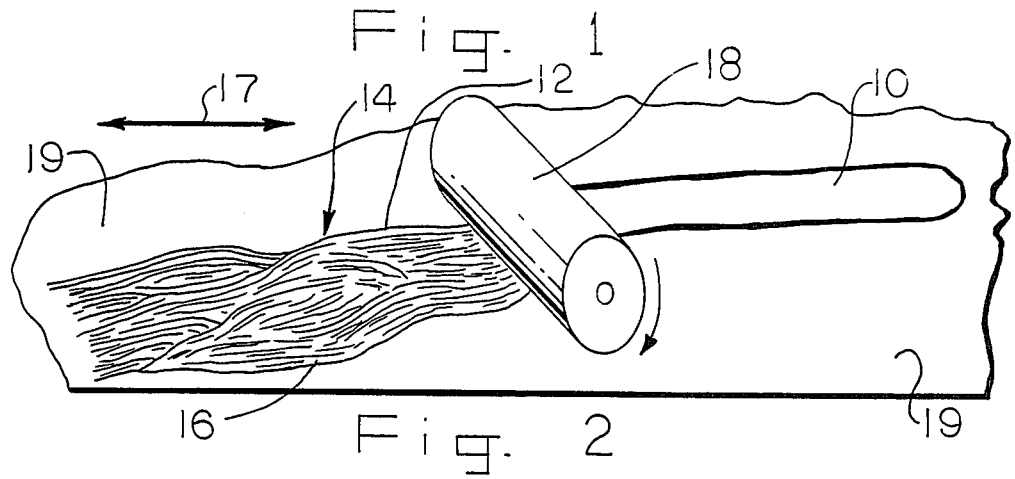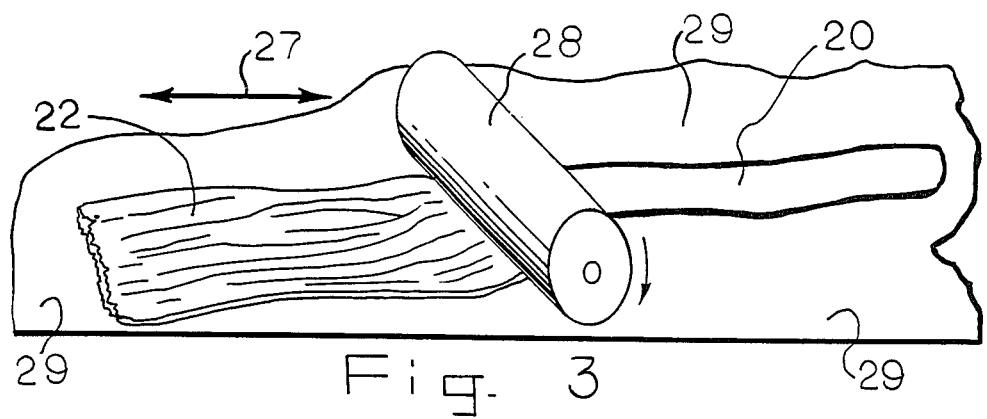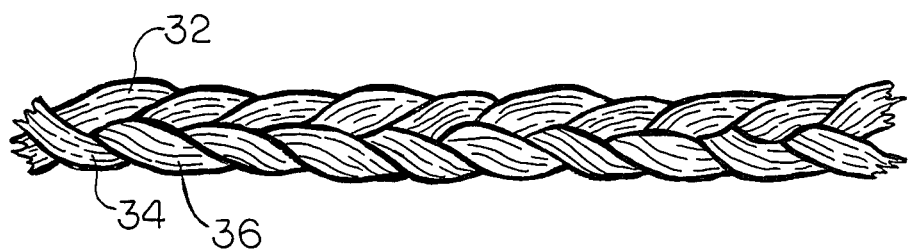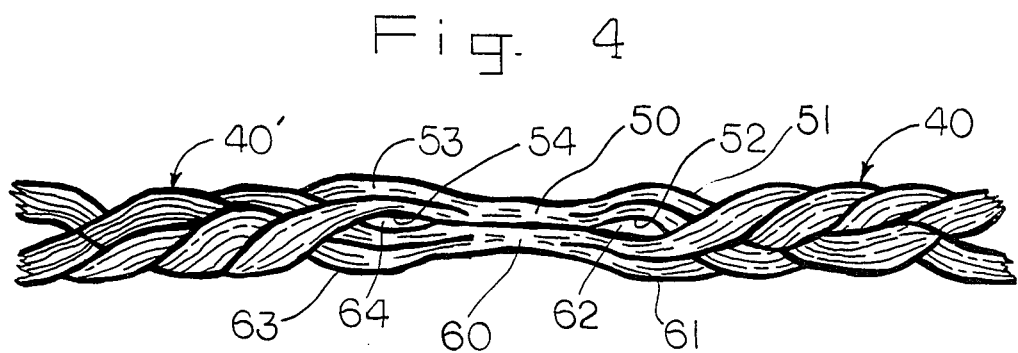

METHOD FOR PRODUCING IMPLANTABLE LIGAMENT AND TENDON PROSTHESES AND PROSTHESES PRODUCED THEREBY

BACKGROUND OF THE INVENTION

This invention relates to a method of preparing collagen-containing tissues for use as surgically implantable prostheses such as ligament or tendon replacements and to the protheses made by such a method.

Collagen in the form of fibers represents the most abundant animal protein in mammals; it accounts for over 30% of all proteins. After being manufactured by the cells, the collagen molecules assemble into very characteristic fibrils. These fibrils vary in diameter from tissue to tissue and with the species and age of the animal. In general they range in diameters between 50 and 400 nanometers and are packed into larger bundles which we call fibers. Between these fibrils and fibers lies an interfibrillar material described in the earlier literature as the "ground substance" which we now believe to be composed of a highly organized network of negatively charged polysaccharides and associated polypeptides referred to as proteoglycans. In some structures, such as in tendons, the bundles of collagen fibers are surrounded by a thin connective tissue network which has not been well characterized biochemically. This composite of collagen and proteoglycans is responsible for the structural integrity of the supportive structures of the body such as skin, bone, tendons, blood vessels, etc. Cross-links between the collagen molecules within the fibrils are a prerequisite for these to be able to withstand the physical stresses to which they are subjected. In humans and animals these cross-links are generated by a rather complicated series of intracellular and extracellular events which generate reactive groups on the surface of the collagen molecules. These proceed to form intramolecular and intermolecular cross-links after the molecules assemble in the extracellular space.

Not all the collagen molecules in a given organism are chemically identical. There is great similarity but nevertheless there are various well-defined types of collagen which in some cases are unique to particular tissues. For instance, the collagen in cartilage differs from that of the cornea, tendon, bone matrix, dermis and most other tissues. There are now nine well-defined types of collagen in vertebrates and many new ones are being discovered. Whereas in certain tissues collagen fibrils are considered to be almost permanent, in others such as bone, which undergoes constant remodeling, collagen is constantly being replaced.

One of the earliest chemical modifications of collagen is associated with the process of leather tanning, a technology that has evolved over the ages. During the last 15 years increased interest has developed in the use of collagen and collagen-containing tissues in the manufacturing of medical devices. In some instances, chemical cross-linking with the use of bifunctional reagents such as glutaraldehyde, generates materials which are readily usable (i.e. pericardial patches). In other cases such as when heart valves are manufactured, porcine aortic valves, following chemical treatment, are mounted on frames or stents in order to provide them with a suitable framework. The stents are often covered with a porous material such as woven DACRON® polyester (DACRON is a trademark of E. I. duPont de Nemours and Company, Wilmington, Del.) to facilitate suturing and tissue ingrowth leading to attachment.

In situations such as tendons and ligaments this type of covering is not very practical because of the magnitude of the forces imposed upon such prostheses. Attaining growth into a DACRON® polyester sleeve, for instance, which is covering a cross-linked tendon-ligament prosthesis as it traverses the bone will not assure the attachment of the ligament per se. If the prosthesis is partially bio-degradable as is the case of some incompletely cross-linked collagen materials, some degradation of the prosthesis and growth of tissue will occur, but the continued resorption and degradation of the intraarticular portion of the prosthesis will lead to eventual failure.

SUMMARY OF THE INVENTION

We have therefore designed an approach to facilitate ingrowth and attachment of native and cross-linked collagenous materials to host tissues. This approach comprises expanding physically the collagenous network of the prosthesis prior to implantation to assure the penetration of host tissue through its interstices in order to ensure attachment and which also provides improved chemical treatment of the tissues.

In accordance with one object of this invention, a means for dissociating the collagen fibrils and fibers present in natural and chemically cross-linked tissues is provided that improves the handling properties of such tissue (flexibility and elasticity) and enhances the potential for tissue ingrowth leading to attachment to the host.

In the process of the present invention, natural collagen-containing tissues such as tendons and ligaments are obtained from animal sources. During the processing of such tissues, the protein structure of the tissues is covalently cross-linked in one step or step-wise to the degree desired to protect the tissue from excessive swelling and other losses of physical integrity after implantation in the body of an animal. The cross-linking comprises treating the tissue with a cross-linking agent, and a permanently implantable prosthesis is constructed from the collagen fiber bundles present in the collagen-containing tissues. At some point prior to implantation, disruption of the interfibrillar soft connective tissues is carried out by a method, such as via the action of a mechanical action of a roller under pressure for providing separation of the collagen fiber bundles that comprise the collagen-containing tissues while retaining substantially all of the natural configuration and length of the individual collagen fibers making up the fiber bundles.

The collagen fibers in native tissues present themselves as a composite of closely packed bundles of fibrils embedded in a proteoglycan matrix. This composite, particularly after the prior art treatments to render it non-biodegradable and antigenic, tends to be resistant to tissue ingrowth and host cell proliferation. As a result of the disruption of this interfibrillar matrix generated by the procedure of the present invention, the collagen fibers become separated in such a way as to generate large interfibrillar spaces suitable for tissue ingrowth. In some tissues, such as the tendon. the collagen fibers are encapsulated by tight fitting connective tissue membranes, as indicated above which in effect form a constraining jacket around the fibers. It has been found that concomitantly with the separation of the collagen fibers according to the present invention, one sees a marked increase in flexibility of the prosthesis. Apparently the release of the fibers from their constraining jacket provides enhanced flexibility of the cross-linked collagen network.

The material so treated is now particularly suitable for use in the production of composites. For instance, several of these natural tissues can be interwoven by weaving or braiding to form larger aggregates of increased cross-section. This provides composites of still more enhanced elasticity. Another aspect of this fiber expansion and dissociation is that it allows the formation of composites between this naturally derived material and synthetic fibers. Such composites should enhance the tensile strength and allow for new modalities for attachment of the prosthesis to bone and soft connective tissues. This modality of treatment also allows for the introduction of other materials into the weave. Degradable fibers can be introduced and intermingled with the natural or cross-linked collagen in such a way that following its resorption, the spaces occupied by such a material will now be replaced by host connective tissue or bone ingrowth.

In addition, the network of collagen fibrils, when separated in accordance with this invention, becomes more readily accessible to any subsequent chemical treatment. Chemicals, in particular cross-linking reagents, penetrate slowly through dense connective tissues such as tendons as becomes evident under many circumstances where fixation is observed to be inadequate or incomplete. This expansion of the fibrillar network prior to completion of chemical treatment is particularly useful when the chemicals to be used are very reactive, of large molecular weight or are unstable in nature. By properly choosing combinations of greatly expanded structure with a less expanded structure and combining other fibers with the naturally derived material, various heretofore unavailable configurations of tendon and ligament prostheses can be obtained. For example, there is described hereinafter a prosthesis specifically designed for replacement of the cruciate ligament of the knee wherein an expanded portion is provided at each end for bone fixation and a relatively smooth center portion is provided for passing through the central knee joint space.

BRIEF DESCRIPTION OF THE DRAWINGS

FIG. 1 illustrates a bovine tendon being mechanically flattened in accordance with this invention after being at least partially fixed and treated by methods described herein.

FIG. 2 shows the effect of mechanical flattening on a tendon before it has been fixed and treated.

FIG. 3 shows three fiber separated tendons braided with each other.

FIG. 4 shows a prosthesis made of two partially expanded tendons made as described herein and divided into two masses each and with the ends braided.

DETAILED DESCRIPTION OF THE INVENTION AND PREFERRED EMBODIMENTS

Exemplary starting materials useful in practicing the invention include animal tissues of diverse origin with relatively long lengths of collagen fibers in the natural state such as are present in ligaments and tendons, which are the preferred starting materials. The tissue used in this invention is required to be in such a state that, to the greatest degree possible, the natural state and length of the collagen fibers is retained.

According to this invention, the tissues are preferably cleaned from adherent fat and loose connective tissue as soon as possible after harvesting, although cleaning may occur after storage or partial processing if more convenient. If other treatments according to the invention are not to be started immediately the tissues are placed for storage in a balanced electrolyte solution that is calcium free and buffered at a neutral pH with a buffer, such as sodium phosphate. This solution is kept cool (e.g., 4°–8° C. in a preferred embodiment).

Several possibilities now exist for further treatment in accordance with the invention. In one embodiment of the invention the tissue is at least partially stabilized by chemical treatment in accordance with prior art processing techniques such as those described, for example, in Nimni et al. U.S. Pat. No. 4,378,224 granted Mar. 29, 1983. The processes described in that patent are incorporated herein by reference, but in a preferred embodiment of this invention comprise treatment of a bovine tendon in a solution containing a conventional cross-linking agent such as a dialdehyde. For example, a 0.2 volume percent aqueous glutaraldehyde solution buffered with phosphate at pH 7.4 may be used. Penetration of glutaraldehyde is enhanced by shaking the solution containing the prosthesis. Since this is a slow process, it is allowed to proceed for at least 7 days with daily changes of the solution. This causes a partial cross-linking of the collagen and the protein-like compounds naturally associated with it.

This tissue is then rinsed with buffered saline (pH 7.4) and extended on a hard surface. A roller device such as a wooden dowel or a metal rolling pin which exerts a downward pressure is moved over the tendon perpendicular to the long axis of the tendon. The amount of pressure used is that amount which is sufficient to mechanically disrupt and thereby cause the fiber bundles of the tissue to separate without destroying the natural configuration and length of the individual collagen fibers. Avoiding such destruction is important because the natural state of the fiber bundles provides strength to the finished prosthesis. The mechanical disruption process is continued until the tendon exhibits a large number of longitudinal striations visible to the naked eye which can be distended laterally by pulling sidewise. For example, a tendon which was originally 6 mm in diameter can be flattened to about 20–30 mm in width. Further details on the mechanical disruption process will become apparent hereinafter.

The disrupted tissue is placed again in the above-described 0.2% glutaraldehyde solution for continued fixation and further treatment in accordance with prior art techniques such as those described in the aforementioned Nimni. et al. patent. This Nimni, et al. procedure incorporates additional covalent cross- links involving the free carboxyl groups of collagen using the carbodiimide reaction and an aliphatic diamine, preferably hexanediamine.

Referring to the Drawings, wherein like reference characters designate corresponding parts throughout the Figures thereof, FIG. 1 shows the manner by which hard roller 18 is used to mechanically disrupt a partially cross-linked bovine extensor longus tendon 10 by placing it against hard flat surface 19 (e.g., a hard table top) and repeatedly drawing roller 18 back and forth in the direction shown by arrows 17 over the tendon 10 and produce portion 12 composed of separated collagen fiber bundles, one of the many present being indicated by reference numeral 16. FIG. 1 further shows the result of distending portion 12 laterally and exerting gentle tension to expose the criss-crossed network of collagen fiber bundles 14 shown which reflects the intricate wavy zig-zag pattern of the native fibrillar structure. After mechanical disrupting, the tendon is further processed chemically as described above. The resulting prosthesis material obtained is characterized by intrafibrillar spaces and by a softer, more flexible nature than the stiff prostheses which are obtained by chemically treating tendons in the same manner, but without including the step of mechanically disrupting the tissue as described herein.

FIG. 2 depicts an alternative embodiment of the present invention showing the effect of mechanically disrupting tendon 20 as described for FIG. 1 above using hard roller 28 in the direction of arrow 27 on hard surface 29. In this embodiment, however, the tendon 20 is used after cleaning but before any further treatment such as fixation by cross-linking is employed. The result shown at 22 is a flattening of the tendon into a compact belt-shaped configuration 22 without as much separation between fibers as can be seen in FIG. 1. The tissue is then fixed in this configuration by chemical processing as has been described above. The mechanical disruption process can also be applied to fully treated collagenous materials while they are in the wet state to obtain softer, more flexible prostheses although this is a less preferred process since the earlier use of the mechanical disruption process exposes more fiber bundles to the chemicals employed to treat the collagenous materials. Applying the mechanical disruption process prior to completion of the chemical treatment tends to eliminate the possibility of untreated areas in the collagenous materials thereby reducing any effects that such untreated portions might have on the performance of the prosthesis after implantation. As a further alternative, and providing still greater assurance of full chemical treatment a first disruption step can be performed, followed by partial chemical treatment and then a further disruption step can be performed before final chemical treatment.

As an alternative to using a single roller against a flat surface, an apparatus composed to two rollers arranged similarly to those of a conventional washing machine roller ringer or a two roll mill where the spacing between the two rollers is adjustable can be used to cause mechanical disruption of the collagen fiber bundles in the tendons. One advantage of using such an apparatus is the fact that the some control can be exerted over the degree of pressure exerted against the tendons by adjusting the roller spacing. The rollers in either case can be made, for example, of hard rubber or stainless steel.

Short, rocking, rolling strokes appear to work better in a mechanical disruption process utilizing a roller than do long continuous strokes. As the diameter of the roller or rollers used is increased, more force against the tendons is needed to achieve the same degree of disruption obtained with smaller diameter rollers.

After the mechanical flattening procedure, the collagen fiber bundles within the tendon may be pulled apart to further increase compliance or to allow separation of long individual fiber bundles. After the mechanical disruption procedure and the fiber separation procedure, the tendons can be reshaped into their natural configuration by gently tugging at the ends.

FIG. 3 depicts the result of braiding masses 32, 34 and 36 of collagen fiber bundles treated in accordance with the process of the present invention to produce a prosthesis 30 which can then be used as, for example, a tendon replacement prosthesis. More than just two masses of treated collagen fiber bundles can be braided. It is also possible to intertwine synthetic polymeric fibers such as DACRON polyester and other biocompatible polymers such as polytetrafluoroethylene, reconstituted collagen fibers (treated or untreated to reduce reabsorption), polylactic acid polymer fibers and the like in with the treated collagen fiber bundles to create composite braided products which have the properties of both types of fibers. Braiding is employed to enhance the physical properties of the prosthesis and to control the diameter of the prosthesis itself.

FIG. 4 depicts a prosthesis which is composed of two mechanically disrupted and chemically treated (in accordance with the present invention) bovine tendons 50, 60 which have been partially expanded into two braided portions 40 and 40' where portion 40 is made by braiding masses 51, 52, 61, and 62 of treated collagen fiber bundles and portion 40' is similarly made by braiding together masses 53, 54, 63 and 64 of treated collagen fiber bundles where the central portions of tendons 50 and 60 are left unbraided.

The processed collagenous materials are then employed in manners known to those skilled in the art of making prostheses from treated collagenous materials to manufacture tendon and ligament prostheses. The embodiment illustrated in FIG. 4 could be used to replace the human cruciate ligament where the opposite ends of the prostheses are stapled or otherwise fixed to the bone and the central portion 50, 60 passes through the central knee joint space.

Although presently preferred embodiments of the invention have been described above, modifications thereof will become apparent to those skilled in the art. Therefore it is to be understood that within the scope of the appended claims the invention may be practiced otherwise than as specifically described.

That which is claimed is:

1. A process for producing implantable prostheses for ligament and tendon replacement comprised of natural collagen-containing tissues where the collagen has a fibrillar protein structure and interfibrillar soft connective tissue binds the collagen fibers together into fiber bundles, which process comprises the steps of:
    A. obtaining collagen-containing tissues from animal sources selected from the group consisting of tendons and ligaments,
    B. treating the tissue with a cross-linking agent to covalently cross-link the protein structure of the natural collagen-containing tissues to the degree desired to protect the tissue from excessive swelling and other losses of physical integrity after implantation in the body of an animal,
    C. constructing a permanently implantable prosthesis from the collagen fiber bundles present in the treated collagen-containing tissues, and at some point during the process prior to completion of said crosslinking,
    D. disrupting the interfibrilllar soft connective tissues to provide separation of the collagen fiber bundles to a degree sufficient to permit penetration of said crosslinking agent around said bundles of said connective tissue to provide treatment of said tissue with the crosslinking agent crosslinking agent while retaining substantially all of the natural configuration and length of the individual collagen fibers making up the fiber bundles.

2. The process as claimed in claim 1 wherein Step (D) is carried out immediately after Step (A), followed by Steps (B) and (C), in that order.

3. The process as claimed in claim 1 wherein Step (B) is carried out in two separate steps comprising Step (B1) which comprises initiating partial cross-linking of the of the protein structure of the natural collagen-containing tissues and Step (B2) comprises completing the desired degree of cross-linking of the natural collagen-containing tissue and Step (D), is carried out between steps (B1) and (B2).

4. The process as claimed in claim 3 wherein Step (D) is carried out twice and the order in which the process is carried out is Step (A), (B1), (D), (B2), (D) followed by (C).

5. The process as claimed in claims 3 or 4 wherein the cross-linking is accomplished using a dialdehyde and Step (B) additionally includes the step of cross-linking the collagen-containing tissue with a water-soluble organic carbodiimide and an aliphatic diamine after Step (B2) is completed.

6. The process as claimed in claim 1 wherein Step (C) comprises weaving the collagen fiber bundles with a second fibrous material.

7. The process as claimed in claim 6 wherein the second fibrous material is a synthetic polymer fiber.

8. The process as claimed in claim 6 wherein the second fibrous material is a fiber of a material which is resorbable upon implantation.

9. A permanently implantable prosthesis made according to the process of claim 1.

10. A permanently implantable prosthesis made according to the process of claim 2.

11. A permanently implantable prosthesis made according to the process of claim 3.

12. A permanently implantable prosthesis made according to the process of claim 4.

13. A permanently implantable prosthesis made according to the process of claim 5.

14. A permanently implantable prosthesis made according to the process of claim 6.

15. A permanently implantable prosthesis made according to the process of claim 7.

16. A permanently implantable prosthesis made according to the process of claim 8.

* * * * *